United States Patent [19]

Gassen

[11] Patent Number: 5,075,494

[45] Date of Patent: Dec. 24, 1991

[54] PROCESS FOR THE PREPARATION OF α-FLUOROACRYLIC ACID DERIVATIVES AND NEW 1,1-DIFLUORO-2-HALOGENOETHYL (HALOGENO) METHYL KETONES

[75] Inventor: Karl-Rudolf Gassen, Odenthal, Fed. Rep. of Germany

[73] Assignee: Bayer Aktiengesellschaft, Leverkusen, Fed. Rep. of Germany

[21] Appl. No.: 514,790

[22] Filed: Apr. 25, 1990

[30] Foreign Application Priority Data

May 13, 1989 [DE] Fed. Rep. of Germany ....... 3915754

[51] Int. Cl.$^5$ .............................................. C07C 69/62

[52] U.S. Cl. .................................... 560/219; 560/213; 560/227; 562/849; 562/859; 562/860; 562/598; 568/419

[58] Field of Search ....................... 560/219, 213, 227; 562/598, 860, 859, 849; 568/419

[56] References Cited

PUBLICATIONS

CA 77(3) 18972t 1972.

Primary Examiner—Paul J. Killos
Attorney, Agent, or Firm—Sprung Horn Kramer & Woods

[57] ABSTRACT

Process for the preparation of α-fluoroacrylic acid derivatives from 2,2-difluoro-1-methyl-cyclopropyl compounds and new 1,1-difluoro-2-halogenoethyl (halogeno)methyl ketones obtainable in this process as intermediates.

6 Claims, No Drawings

PROCESS FOR THE PREPARATION OF α-FLUOROACRYLIC ACID DERIVATIVES AND NEW 1,1-DIFLUORO-2-HALOGENOETHYL (HALOGENO) METHYL KETONES

The present invention relates to an advantageous process for the preparation of α-fluoroacrylic acid derivatives and 1,1-difluoro-2-halogenoethyl (halogeno)-methyl ketones which are obtainable as intermediates in this process.

Derivatives of α-fluoroacrylic acid are versatile organic intermediates and can be used in particular as monomers for the preparation of polymers for optical glasses, light waveguides and their coverings (see, for example, EP-A 0,128,517). The processes known hitherto for the preparation of α-fluoroacrylic acid derivatives are disadvantageous as they require many reaction steps, result in poor yields, require poorly accessible and, to some extent, toxic chemicals whose handling requires special expenditure in terms of safety, are not reproducible and/or only permit the preparation of small quantities.

It has thus hitherto been known to prepare 2-fluoroacryloyl fluoride from tetrafluorooxetane (see EP-OS (European Published Specification) 0,148,490), which is only accessible with great technical difficulty and is very toxic. The synthesis starting from fluoroacetic acid has the same disadvantages (see U.S. Pat. No. 3,075,002). A process which starts from 1,2-dibromo-3-chloropropane requires many reaction steps (see Zh. Org. Khim. 28, 1173 (1987)). An electrochemical preparation method (see DE-A 3,704,915) requires a large expenditure in terms of apparatus and does not always yield reproducible results.

The need therefore exists for a process, which is effective and can be carried out simply, for the preparation of α-fluoroacrylic acid derivatives in industrial quantities.

A process has now been found for the preparation of α-fluoroacrylic acid derivatives of the formula (I)

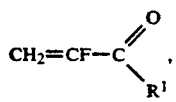

in which
R$^1$ represents a fluorine atom, a chlorine atom or OR$^2$, where R$^2$ = optionally substituted C$_1$- to C$_{20}$-alkyl, optionally substituted C$_3$- to C$_{20}$-cycloalkyl, optionally substituted C$_6$- to C$_{20}$-aryl or optionally substituted C$_7$- to C$_{20}$-aralkyl, which is characterized in that a 2,2-difluoro-1-methyl-cyclopropyl compound of the formula (II)

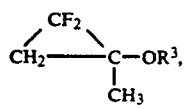

in which
R$^3$ represents C$_1$- to C$_6$-alkyl or C$_2$- to C$_6$-acyl,
is reacted with at least one equivalent of halogen from the group comprising chlorine, bromine and iodine and compounds are thus obtained of the formula (III)

in which
n represents 0, 1, 2 or 3 and
Hal in each case independently of one another represents chlorine, bromine or iodine, this is reacted with further halogen in the presence of aqueous alkali to give the corresponding carboxylic acid of the formula (IV)

in which
Hal represents chlorine, bromine or iodine,
this is converted in a manner known per se into the corresponding acid chloride of the formula (V)

in which
Hal represents chlorine, bromine or iodine,
for the preparation of compounds of the formula (I) where R$^1$=OR$^2$, the acid chloride of the formula (V) is esterified with an alcohol of the formula HOR$^2$ to give an ester of the formula (VI)

in which
Hal represents chlorine, bromine or iodine and
R$^2$ has the meaning given in formula (I),
and the acid chloride of the formula (V) or the ester of the formula (VI) is partially dehalogenated.

If, in the α-fluoroacrylic acid derivatives of the formula (I), R$^2$ represents an optionally substituted alkyl, cycloalkyl, aryl or aralkyl radical, suitable substituents are, for example, halogen atoms, C$_1$- to C$_6$-alkoxy radicals, C$_6$- to C$_{10}$-aryloxy radicals, C$_7$- to C$_{12}$-aralkoxy radicals and/or 5- or 6-membered heterocyclic radicals such as pyridyl, pyrimidyl and imidazoyl. Preferred radicals are unsubstituted radicals and radicals substituted by halogen atoms, in particular by fluorine and/or chlorine, of the type mentioned. Preferably, in formula (I), R$^1$ represents a fluorine atom or OR$^2$, where R$^2$ denotes C$_1$- to C$_6$-alkyl optionally substituted by fluorine and/or chlorine, C$_3$- to C$_6$-cycloalkyl optionally substituted by fluorine and/or chlorine, C$_6$-to C$_{10}$-aryl optionally substituted by fluorine and/or chlorine or C$_7$- to C$_{10}$-aralkyl optionally substituted by fluorine and/or chlorine. Fluorine is particularly preferred as a substituent. The number of substituents can vary widely. Highly substituted radicals are preferred, in particular those having a degree of fluorination of 50 to 100%.

The 2,2-difluoro-1-methyl-cyclopropyl compounds of the formula (II) required as starting compounds for the process according to the invention are known and easily accessible (see Chem. Ber. 109, 2351 (1976) and Chem. Pharm. Bull. 27, 3123 (1979)). Compounds of the formula (II) are preferably employed in which R$^3$ represents methyl, ethyl or acetyl, particularly preferably those where R$^3$=methyl.

At least one equivalent of halogen from the group comprising chlorine, bromine and iodine, preferably bromine, is employed for the reaction to give compounds of the formula (III). This ensures an extensive to complete cleavage of the cyclopropyl ring. Using approximately one equivalent of halogen, for example 1.0 to 1.2 equivalents, the compound of the formula (III)

where $n=0$ is predominantly obtained. If larger amounts of halogen are employed, compounds of the formula (III) where $n=1$, 2 or 3 are predominantly obtained. From economical considerations, it is in general advantageous to employ not more than 6 equivalents of halogen.

The reaction is in general carried out in the presence of a diluent, for example in the presence of an organic solvent or water. Water is preferred, care expediently being taken to mix the reaction mixture thoroughly. The reaction temperature is not critical and may be, for example, 0° to 50° C. The reaction is preferably carried out at 18° to 25° C.

It is not necessary to isolate the compound of the formula (III) prepared in this way or the mixture of compounds of the formula (III) prepared in this way, especially if water has been employed as a diluent.

The next reaction step, the conversion of the compound(s) of the formula (III) into the carboxylic acid of the formula (IV) can be carried out in the same vessel as the reaction with halogen described above. For this purpose, only at least as much halogen need be present, if appropriate as a result of a fresh addition, as is theoretically required for the quantitative formation of the compound of the formula (III) where $n=3$ and for its cleavage to give the carboxylic acid of the formula (IV) and the respective haloform. For the halogenation to (the) compound(s) of the formula (III) and its (their) cleavage to the carboxylic acid of the formula (IV) and haloform, altogether 4 equivalents of halogen are theoretically required. Altogether therefore, for example, 3.8 to 6, preferably 4.0 to 5.5 equivalents of halogen are employed, it being possible to employ, for example, 1 to 3.2 equivalents in the reaction with the cyclopropyl compound of the formula (II) and, for example, 2.8 to 5 equivalents in the reaction for the preparation of the carboxylic acid of the formula (IV). The halogen or excess halogen required in total can also even be employed for the reaction of the cyclopropyl compound of the formula (II). If halogen is added two or more times, the halogen may in each case be identical or different, for example only bromine, but also, for example, first bromine and then chlorine. Chlorine can be reacted, for example, in elemental form or in the form of a hypochlorite solution.

The conversion of the compound(s) of the formula (III) into the carboxylic acid of the formula (IV) can be performed, for example, at 0° to 50° C. The conversion is preferably carried out at 18° to 25° C. The haloform formed as the second product in this case can be recovered from the reaction mixture in pure form, for example by distillation, and is then utilizable in a known manner, for example if it is bromoform, for the separation of mineral mixtures of as a calibrating fluid.

The aqueous-alkaline medium required for the reaction of the compound(s) of the formula (III) to give the carboxylic acid of the formula (IV) can be prepared, for example, by addition of aqueous alkali, for example aqueous sodium hydroxide or potassium hydroxide solution. For example, a quantity of alkali can be added such that, during and after the reaction, the pH is in the range from 8 to 14.

The carboxylic acid of the formula (IV) can be isolated, for example, from the reaction mixture by acidifying the reaction mixture, for example with mineral acid and separating off the organic phase and distilling.

The conversion of the carboxylic acid of the formula (IV) into the corresponding carboxylic acid chloride of the formula (V) can be carried out in a manner known per se, for example by reaction with phosphorus trichloride, phosphorus pentachloride, sulphuryl chloride or thionyl chloride. A small excess of thionyl chloride is preferably used at temperatures in the range from 15° to 80° C. The acid chloride of the formula (V) may optionally be isolated by direct distillation.

If it is wished to prepare $\alpha$-fluoroacrylic acid derivatives of the formula (I) where $R^1=OR^2$, esterification with an alcohol of the formula $R^2OH$ is added to the preparation of the carboxylic acid chloride of the formula (V). The alcohol is expediently chosen in this case such that its $R^2O$ radical corresponds to the radical $R^1$ in the compound of the formula (I) which it is wished to prepare. Later transesterification reactions are thus unnecessary. Alcohols of the formula $R^2OH$ are easily accessible, in particular those alcohols of the formula $R^2OH$ in which $R^2$ has the meanings given as preferred in formula (I). The esterification may be carried out in a manner known per se, for example by warming the acid chloride and the alcohol, if appropriate in the presence of a diluent. After customary working up, an ester of the formula (VI) can thus be obtained.

Some esters of the formula (VI), for example where Hal=bromine and $R^2$=ethyl, are known. They were prepared by fluorination of 3-bromopyruvic acid esters with sulphur tetrafluoride (see J. Med. Chem. 31, 370 (1988)). Owing to the large expenditure in terms of safety for the handling of sulphur tetrafluoride, this process is in any case only utilizable on the laboratory scale and thus far inferior to the process according to the invention.

In order to prepare $\alpha$-fluoroacrylic acid derivatives of the formula (I) where $R^1=OR^2$, the ester of the formula (VI), for the preparation of $\alpha$-fluoroacrylic acid derivatives of the formula (I) where $R^1$=fluorine or chlorine the carboxylic acid chloride of the formula (V) are to be partially dehalogenated. This partial dehalogenation can be carried out electrochemically or with chemical dehalogenating agents. Chemical dehalogenating agents are, for example, metal halides in which the metal is present in a low oxidation state, for example $CrCl_2$, and metals, for example magnesium, iron or zinc. Zinc, which may optionally be activated, is preferably used (see L. F. Fieser and M. Fieser, Reagents for Org. Synth., Wiley, Vol 1, p. 1276 (1967)). The reaction is customarily carried out in the presence of a diluent. Those which are suitable are, for example, various glymes, tetrahydrofuran, dioxane, water and any mixtures thereof Suitable temperatures are, for example, those from 20° to 250° C., in particular those from 50° to 200° C.

A preferred embodiment of the partial dehalogenation consists in reacting the carboxylic acid chloride of the formula (V) with zinc at 80° to 110° C. in the presence of diglyme and distilling off the $\alpha$-fluoroacrylic acid derivative of the formula (I) where $R^1$=fluorine or chlorine formed in this way. It is surprising here that, during the partial dehalogenation, exchange of halogen can take place, in particular if a relatively long residence time is realized by relatively slow dropwise addition of the carboxylic acid chloride of the formula (V) and relatively slow removal of the reaction product by distillation (which can be controlled by means of temperature and/or pressure. The $\alpha$-fluoroacryloyl fluoride (formula (I), $R^1=F$) is preferably thus obtained from a carboxylic acid chloride of the formula (V). With relatively rapid dropwise addition of the carboxylic acid chloride of the formula (V) and relatively rapid removal of the reaction products by distillation, α-fluoroacryloyl chloride (formula (I), $R^1=Cl$) is preferably obtained If mixtures of α-fluoroacryloyl fluoride and chloride are obtained, these can be separated by distillation.

Another preferred embodiment of the partial dehalogenation consists in reacting an ester of the formula (VI) with zinc at 50° to 100° C. in the presence of water and removing water and the resultant α-fluoroacrylic acid derivative of the formula (I) where $R^1=OR^2$, from the reaction mixture by distillation. The α-fluoroacrylic acid derivative can be recovered in pure form from the distillate by customary methods, for example by phase separation and drying and distillation of the organic phase. It is advantageous to keep the pH of the reaction mixture between 7 and 2 during the reaction by addition of an acid, for example dilute sulphuric acid.

As the α-fluoroacrylic acid derivatives of the formula (I) are frequently sensitive to polymerization, it is in general recommended to add customary polymerization inhibitors, for example 4-methoxyphenol, during their preparation and storage.

The present invention permits the preparation of α-fluoroacrylic acid derivatives in a simple manner, in a few reaction steps (the conversion of the starting material of the formula (II) to the carboxylic acid of the formula (IV) can be carried out as a one-pot reaction), with good yields, using chemicals which have little or no toxicity and in customary apparatus. It is therefore particularly suitable for the preparation of α-fluoroacrylic acid derivatives in industrial quantities.

The present invention furthermore relates to new 1,1-difluoro-2-halogenoethyl (halogeno)methyl ketones of the formula (IIIa)

   (IIIa), in which
 n represents 0, 1, 2 or 3,
 Hal represents chlorine, bromine or iodine and
 if n=1, 2 or 3, Hal, represents chlorine, bromine or iodine and
 if n=0, Hal' represents bromine
The compounds are, in this case, for example
1,1-difluoro-2-bromoethyl methyl ketone,
1,1-difluoro-2-bromoethyl halogenomethyl ketones,
1,1-difluoro-2-bromoethyl dihalogenomethyl ketones,
1,1-difluoro-2-bromoethyl trihalogenomethyl ketones,
1,1-difluoro-2-chloroethyl halogenomethyl ketones,
1,1-difluoro-2-chloroethyl dihalogenomethyl ketones,
1,1-difluoro-2-chloroethyl trihalogenomethyl ketones,
1,1-difluoro-2-iodoethyl halogenomethyl- ketones,
1,1-difluoro-2-iodoethyl dihalogenomethyl ketones and
1,1-difluoro-2-iodoethyl trihalogenomethvl- ketones,
halogen in each case denoting chlorine, bromine or iodine.

Preferred compounds of the formula (IIIa) are those in which n represents 0, 1 or 2, Hal represents chlorine or bromine and Hal' represents bromine, that is, for example,
1,1-difluoro-2-bromoethyl bromomethyl ketone,
1,1-difluoro-2-bromoethyl dibromomethyl ketone and
1,1-difluoro-2-bromoethyl methyl ketone The preparation of compounds of the formula (IIIa) can be carried out as described above. It is to be considered here that with the amount of halogen which is allowed to act on the 2,2-difluoro-1-methyl-cyclopropyl compound of the formula (I), it is possible to control whether 1,1-difluoro-2-halogenoethyl (halogeno)methyl ketones of the formula (III) where n=0, 1, 2 or 3 are predominantly formed. If, for example, 1.0 to 1.2 equivalents of halogen are employed, the compound of the formula (IIIa) where n=0 is predominantly formed. Correspondingly, compounds of the formula (IIIa) where n=1, 2 or 3 are predominantly formed if, for example, 1.8 to 2.2 or 2.8 to 3.2 or 3.8 to 4.2 equivalents of halogen are employed respectively. The compounds of the formula (IIIa) can be isolated from the reaction mixture, for example, by separating off the organic phase and, if appropriate, distilling after drying It may be advantageous to remove excess halogen, which may still be present, before the distillation, for example by shaking with a hydrogen sulphite solution.

The compounds of the formula (III) can be used, as described above, as intermediates for the preparation of α-fluoroacrylic acid derivatives which, for their part, are monomers for the preparation of polymers which are used, for example, for optical glasses, light waveguides and their coverings.

EXAMPLE 1

45 g (0.37 mol) of 2,2-difluoro-1-methylcyclopropyl methyl ether, 240 g (1.5 mol) of bromine and 300 ml of water were stirred for 18 hours at room temperature. The mixture was then extracted with diethyl ether, the organic phase was dried and 85.5 g (67% of theory) of a product of the formula (III) where n=2 and Hal=-bromine were isolated, which boiled at 20 mbar at 101° to 103° C., displayed the C=O absorption at 1770 cm$^{-1}$ in the IR spectrum, showed H-NMR absorptions at 3.79 and 6.40 ppm, and generated the isotope pattern of the molecular ion with 3 bromine atoms at m/e 342, 344 and 346 in the MS spectrum.

EXAMPLE 2

The procedure was as in Example 1, but only 0.5 mol of bromine was employed and the product of the formula (III) where n=1 and Hal=bromine was obtained, which generated the isotope pattern of the molecular ion with 2 bromine atoms at m/e 264 and 266 in the MS spectrum.

EXAMPLE 3

71 g (1 mol) of chlorine were passed into a mixture of 122 g (1 mol) of 2,2-difluoro-1-methylcyclopropyl methyl ether and 700 ml of water and the procedure was otherwise as in Example 1. 37 g (26 % of theory) of the product of the formula (III) where n=0 and Hal=-chlorine were obtained, which boiled at 104° to 105° C. (at normal pressure), displayed the C=O absorption at 1740 cm$^{-1}$ in the IR spectrum and showed $^1$H-NMR absorptions at 2.41 and 3.87 ppm.

EXAMPLE 4

The procedure was analogous to the procedure of Example 1 using a mixture of 12 g (0.1 mol) of 2,2-difluoro-1-methylcyclopropyl methyl ether, 70 ml of water and 40 g (0.16 mol) of iodine. 2.5 g (11% of theory) of the product of the formula (III) wherein n=0 and Hal=iodine were obtained, which displayed the C=O absorption at 1745 cm$^{-1}$ in the IR spectrum and gave characteristic signals, inter alia, at m/e=234, 191/190, 127, 64 and 43 in the mass spectrum.

EXAMPLE 5

45 g (0.37 mol) of 2,2-difluoro-1-methylcyclopropyl methyl ether were stirred at room temperature for 18 hours with 300 g (1.88 mol) of bromine and 300 ml of water. 10 mol equivalents of 45% strength sodium hydroxide solution were then added dropwise with ice-cooling and the mixture was stirred for a further 15 hours. The mixture was then removed by shaking with sodium hydrogen sulphite solution, acidified with concentrated hydrochloric acid and extracted with diethyl ether. After drying the organic phase, 44.8 g (64 % of theory) of pure acid of the formula (IV) where Hal=bromine were obtained by distillation, which boiled at 18 mbar at 90° C., displayed a melting point of 49° to 50° C., showed the C=O absorption at 1760 cm$^{-1}$ in the IR spectrum and gave resonances at 3.78 and 10.28 ppm in the H-NMR spectrum.

EXAMPLE 6

The procedure was as in Example 5, but the compound of the formula (III) where n=2 and Hal=bromine (preparation see Example 1) and 2.5 equivalents of bromine were employed as starting materials. In this manner, the compound of the formula (IV) where Hal=bromine was likewise obtained, but this time in a yield of 79% of theory.

EXAMPLE 7

50 g (0.26 mol) of 3-2,2-difluoro-pripionic acid and 37.5 g (0.32 mol) of thionyl chloride were stirred at room temperature until evolution of gas was complete and then distilled directly. 46 g (84% of theory) of the compound of the formula (V) where Hal=bromine were obtained, which displayed a boiling point of 111° to 112° C. (at normal pressure), and which showed the C=O absorption at 1790 cm$^{-1}$ in the IR spectrum and produced a triplet at 3.79 ppm in the $^1$H-NMR spectrum.

EXAMPLE 8

19 g (0.091 mol) of 3-bromo-2,2-difluoropropionyl chloride and 60 ml of ethanol were heated to reflux for 3 hours. The mixture was then diluted with water, extracted with dichloromethane, and the organic phases were freed from acid, dried and distilled. 14.5 g (73% of theory) of a compound of the formula (VI) where Hal=bromine and R$^2$=ethyl were thus obtained, which boiled at 65 mbar at 78° to 80° C. and displayed the C=O absorption at 1760 cm$^{-1}$ in the IR spectrum.

EXAMPLE 9

53 g (0.25 mol) of 3-bromo-2,2-difluoro-propionyl chloride were added dropwise to a suspension of 25 g (0.38 mol) of zinc and 50 ml of diglyme, which was warmed to 100° C. During the dropwise addition, a part of the product was already removed by distillation. In order to complete the conversion, the bath temperature was increased to 170° C. and further product was thus removed by distillation. Altogether, 15 g (65% of theory) of the compound of the formula (I) where R$^1$=fluorine were obtained, which boiled at 29° to 31° C. (at normal pressure) and displayed the C=O absorption at 1830 cm$^{-1}$ in the IR spectrum.

EXAMPLE 10

Example 9 was repeated, the product being removed by distillation through a less highly effective column. In this case, the product contained a small amount of α-fluoroacryloyl chloride.

EXAMPLE 11

5 g (0.023 mol) of ethyl 3-bromo-2,2-difluoropropionate were added dropwise to a suspension of 5 g (0.077 mol) of zinc, 10 ml of water and 250 mg of concentrated sulphuric acid, which was warmed to 100° C. The product was removed by distillation in this case as an azeotrope in a receiver which contained 10 mg of 4-methoxyphenol. By means of phase separation and drying, 1.5 g (55% of theory) of pure compound of the formula (I) where R$^1$=OR$^2$ where R$^2$=ethyl were obtained, which displayed absorptions at 1.36, 4.38, 5.31 and 5.68 ppm in the $^1$H-NMR spectrum.

What is claimed is:

1. A process for the preparation of α-fluoroacrylic acid derivatives of the formula (I)

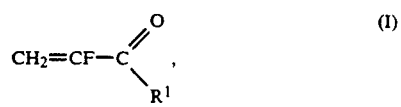

in which
R$^1$ represents a fluorine atom, a chlorine atom or OR$^2$ where R$^2$=unsubstituted or substituted C$_1$- to C$_{20}$-alkyl, unsubstituted or substituted C$_3$- to C$_{20}$-cycloalkyl, unsubstituted or substituted C$_6$- to C$_{20}$-aryl or unsubstituted or substituted C$_7$- to C$_{20}$-aralkyl, the substituents when present being selected from the group consisting of halogen, C$_1$-C$_6$-alkoxy, C$_6$-C$_{16}$-aryloxy, C$_7$-C$_{12}$-aralkoxy, pyridyl, pyrimidyl and imidazolyl, in which a 2,2-difluoro-1-methyl-cyclopropyl compound of formula (II)

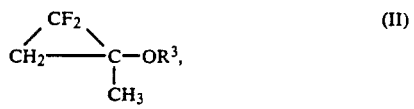

in which
R$^3$ represents C$_1$- to C$_6$-alkyl or C$_2$- to C$_6$-acyl, is reacted with at least one equivalent of halogen from the group comprising chlorine, bromine and iodine in the presents of a diluent at 0° to 50° C. and compounds are thus obtained of the formula (III)

in which
n represents 0, 1, 2 or 3 and
Hal in each case independently of one another represents chlorine, bromine or iodine, this is reacted with further halogen in the presents of aqueous alkali at 0 to 50° C. to give the corresponding carboxylic acid of the formula (IV)

in which
Hal represents chlorine, bromine or iodine,
this is converted by reaction with phosphorus trichloride, phosphorus pentachloride, sulphonyl chloride or thionyl chloride at 15° to 80° C. into the corresponding acid chloride of the formula (V)

$HalCH_2-CF_2-COCl$ (V), in which

Hal represents chlorine, bromine or iodine, for the preparation of compounds of the formula I(I) where $R^1-=OR^2$, the acid chloride of the formula (V) is esterified with an alcohol of the formula $HOR_2$ to give an ester of the formula (VI)

$HALCH_2-CF_2-COOR^2$ (VI)

in which

Hal represent chlorine, bromine or iodine and $R_2$ has the meaning given in formula (I), and the acid chloride of the formula (V) or the ester of the formula (VI) is partially dehalogenated by means of an electrochemical dehalogenation or by means of chemical dehalogenation with $CrCl_2$, magnesium, iron or zinc in the presence of a diluent at 20° to 250° C.

2. The process of claim 1, in which bromine is used as the halogen.

3. The process of claim 1, in which zinc is used as the dehalogenating agent.

4. The process of claim 1, in which compounds of the formula (1), in which $R^1$ represents a fluorine atom or a chlorine atom, are prepared by reacting a 2,2-difluoro-1-methyl-cyclopropyl compound of the formula (II)

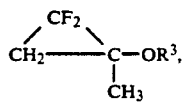 (II)

in which $R^3$ represents $C_1$- to $C_6$-alkyl or $C_2$- to $C_6$-acyl, with at least one equivalent of halogen from the group comprising chlorine, bromine and iodine and compounds are thus obtained of the formula (III)

$HalCH_2-CF_2-CO-CH_{3-n}Hal_n$ (III), in which n represents 0, 1, 2 or 3 and

Hal in each case independently of one another represents chlorine, bromine or iodine, reacting this with further halogen in the presence of aqueous alkali to give the corresponding carboxylic acid of the formula (IV)

$HalCH_2-CF_2-COOH$ (IV), in which

Hal represents chlorine, bromine or iodine, converting this in a manner known per se into the corresponding acid chloride of the formula (V)

$HalCH_2-CF_2-COCl$ (V), in which

Hal represents chlorine, bromine or iodine, and partially dehalogenating the acid chloride of the formula (V).

5. The process of claim 4, in which compounds of the formula (I), in which $R^1$ represents a fluorine atom, are prepared by slowly adding the acid chloride of the formula (V) dropwise to the dehalogenation and slowly removing the reaction products by distillation.

6. A 1,1-difluoro-2-halogenoethyl- (halogeno)methyl ketone selected from the group consisting of
1,1-difluoro-2-bromoethyl bromomethyl ketone,
1,1-difluoro-2-bromoethyl dibromomethyl ketone and
1,1-difluoro-2-bromoethyl methyl ketone.

* * * * *

UNITED STATES PATENT AND TRADEMARK OFFICE
CERTIFICATE OF CORRECTION

PATENT NO. : 5,075,494
DATED : December 24, 1991
INVENTOR(S) : Karl-Rudolf Gassen It is certified that error appears in the above-identified patent and that said Letters Patent is hereby corrected as shown below:

Col. 8, line 47    Delete " presents " and substitute -- presence --

Col. 9, line 5     Delete " I(I) " and substitute -- (I) --

Col. 9, line 10    Delete " $HALCH_2-CF_2-COOR^2$ " and substitute -- $HalCH_2-CF_2-COOR^2$ --

Signed and Sealed this

Sixth Day of July, 1993

*Attest:*

MICHAEL K. KIRK

*Attesting Officer*    Acting Commissioner of Patents and Trademarks